(12) United States Patent (10) Patent No.: US 7,682,820 B2
Bader (45) Date of Patent: Mar. 23, 2010

(54) DEVICE FOR PRESSURIZED PERFUSION ESPECIALLY FOR CULTURING AND/OR TREATING CELLS

(76) Inventor: Augustinus Bader, Krankenhausstrasse 7, Parenthenstein Ot Klinga (DE) D-04668

( * ) Notice: Subject to any disclaimer, the term of this patent is extended or adjusted under 35 U.S.C. 154(b) by 9 days.

(21) Appl. No.: 12/055,808

(22) Filed: Mar. 26, 2008

(65) Prior Publication Data

US 2008/0227189 A1 Sep. 18, 2008

Related U.S. Application Data

(62) Division of application No. 10/482,072, filed as application No. PCT/EP02/07025 on Jun. 25, 2002, now Pat. No. 7,378,271.

(30) Foreign Application Priority Data

Jun. 25, 2001 (DE) .................................. 101 30 512

(51) Int. Cl.
*C12M 1/00* (2006.01)
*C12M 3/00* (2006.01)
(52) U.S. Cl. .................................................. 435/289.1
(58) Field of Classification Search .............. 435/289.1; 417/415–418, 435
See application file for complete search history.

(56) References Cited

U.S. PATENT DOCUMENTS

| | | | |
|---|---|---|---|
| 2,269,857 A * | 1/1942 | Nielsen | 417/390 |
| 4,512,726 A | 4/1985 | Strimling | |
| 4,557,673 A | 12/1985 | Chen et al. | |
| 4,584,994 A | 4/1986 | Bamberger et al. | |
| 4,792,603 A | 12/1988 | Saegusa et al. | |
| 4,889,812 A | 12/1989 | Guinn et al. | |
| 5,010,013 A | 4/1991 | Serkes et al. | |

(Continued)

FOREIGN PATENT DOCUMENTS

DE 1945805 3/1971

(Continued)

OTHER PUBLICATIONS

Simon P. Hoerstrup et al.: "New Pulsatile Bioreactor for In Vitro Formation of Tissue Engineered Heart Valves", Tissue Engineering, vol. 6, No. 1, 2000, pp. 75-79.

(Continued)

*Primary Examiner*—Walter D Griffin
*Assistant Examiner*—Shanta G Doe
(74) *Attorney, Agent, or Firm*—Laurence A. Greenberg; Werner H. Stemer; Ralph E. Locher

(57) ABSTRACT

The invention relates to a device for pumping a fluid into a bioreactor. Polsatile pumping is made possible by valve arrangement so that growth of the cells in the bioreactor is increased. Pumping function can be achieved though several mechanisms. A piston can be displaced in a cylinder, especially by an electromagnet, wherein a permanent magnet or likewise an electromagnet can be arranged in the piston. The piston can also be displaced by compressed air. An elastic, hollow body can also be provided, wherein said hollow body can be deformed by mechanical electromagnetic forces so that pumping function is achieved by a change in volume. The pumping device can also be used as implant for assisting or replacing heart function.

7 Claims, 17 Drawing Sheets

U.S. PATENT DOCUMENTS

| | | |
|---|---|---|
| 5,085,563 A | 2/1992 | Collins et al. |
| 5,205,819 A | 4/1993 | Ross et al. |
| 5,637,936 A | 6/1997 | Meador |
| 5,792,603 A | 8/1998 | Dunkelman et al. |
| 5,846,828 A | 12/1998 | Peterson et al. |
| 5,899,937 A | 5/1999 | Goldstein et al. |
| 5,928,945 A | 7/1999 | Seliktar et al. |
| 6,050,787 A | 4/2000 | Hesketh |
| 6,060,306 A | 5/2000 | Flatt et al. |
| 6,071,088 A | 6/2000 | Bishop et al. |
| 6,121,042 A | 9/2000 | Peterson et al. |
| 6,209,552 B1 | 4/2001 | Dobbelaar et al. |
| 6,379,956 B1 | 4/2002 | Bader |
| 2004/0208761 A1 | 10/2004 | Bader |

FOREIGN PATENT DOCUMENTS

| | | |
|---|---|---|
| DE | 3641260 A1 | 6/1988 |
| DE | 3715952 A1 | 11/1988 |
| DE | 3810843 C2 | 10/1989 |
| DE | 3914956 A1 | 11/1990 |
| DE | 19504751 A1 | 8/1996 |
| DE | 19506183 C1 | 8/1996 |
| DE | 19801763 C2 | 7/1999 |
| DE | 19915610 A1 | 10/2000 |
| DE | 19935643 A1 | 2/2001 |
| DE | 10058240 A1 | 5/2002 |
| EP | 0320348 A1 | 6/1989 |
| EP | 0320441 A1 | 6/1989 |
| EP | 0638641 A1 | 2/1995 |
| EP | 1027898 A1 | 8/2000 |
| GB | 898750 | 6/1962 |
| JP | 60043188 A | 3/1985 |
| WO | 9749799 | 12/1997 |
| WO | 0059560 | 10/2000 |
| WO | 0104909 A1 | 1/2001 |

OTHER PUBLICATIONS

L.E. Niklason et al.: "Functional Arteries Grown in Vitro", Science, vol. 284, Apr. 16, 1999, pp. 489-493.

* cited by examiner

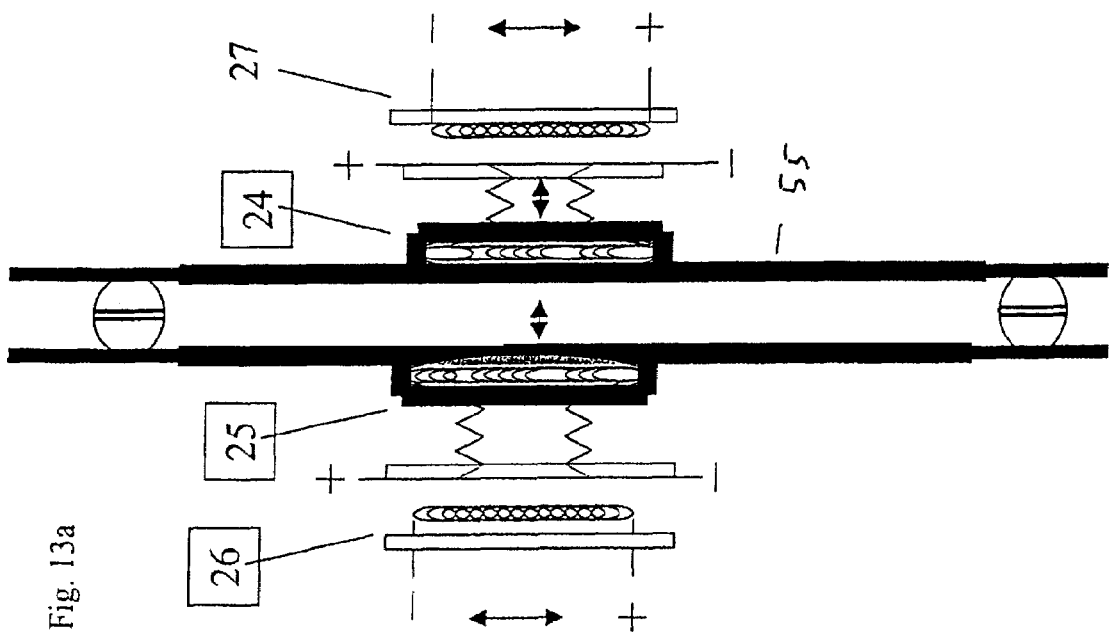
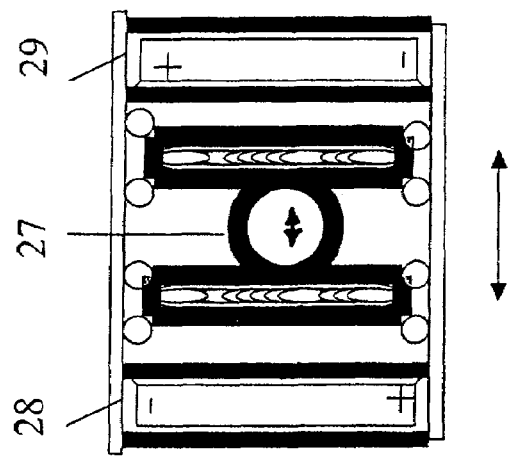
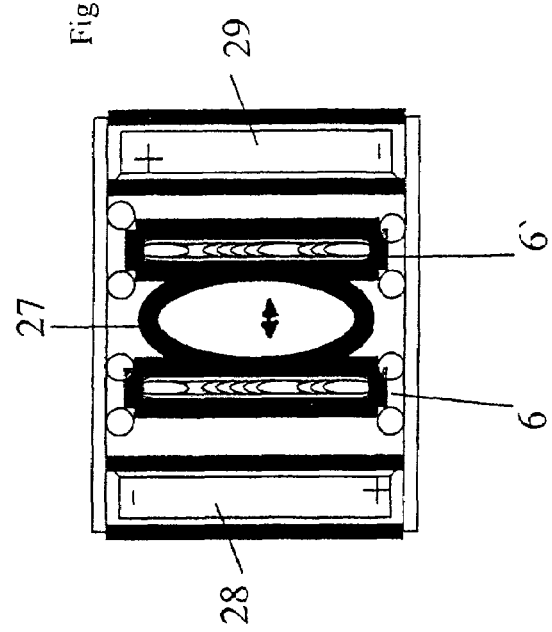

Fig. 15
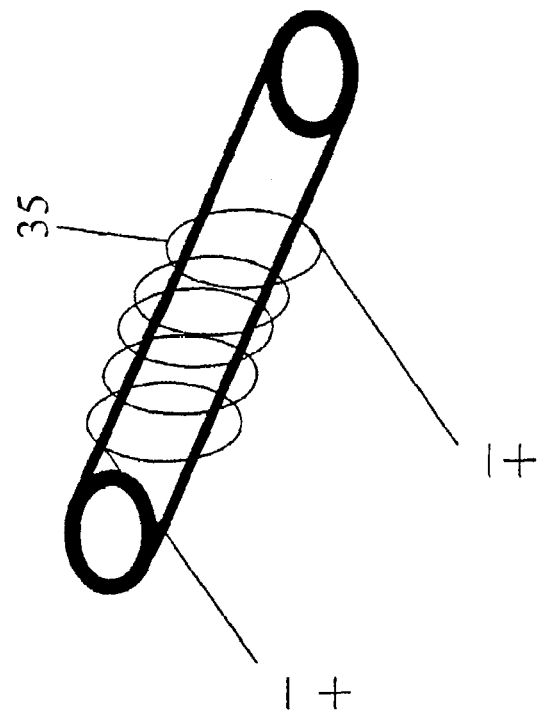
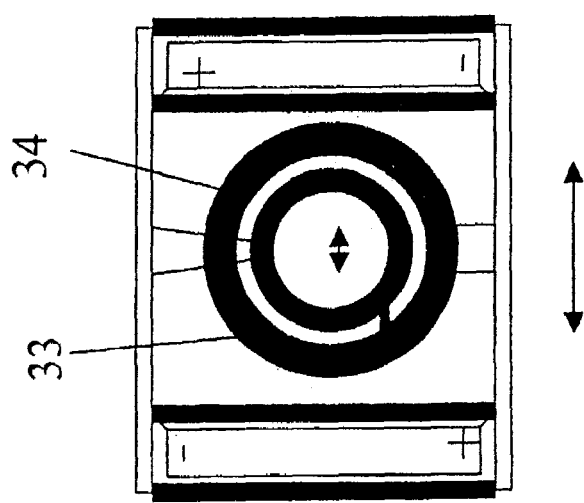

DEVICE FOR PRESSURIZED PERFUSION ESPECIALLY FOR CULTURING AND/OR TREATING CELLS

CROSS-REFERENCE TO RELATED APPLICATION

This is a divisional application of application Ser. No. 10/482,072, filed Dec. 24, 2003; which was a §371 national stage of International application PCT/EP02/07025, filed Jun. 25, 2002; the application also claims the priority, under 35 U.S.C. §119, of German patent application No. 101 30 512.5, filed Jun. 25, 2001; the prior applications are herewith incorporated by reference in their entirety.

BACKGROUND OF THE INVENTION

Field of the Invention

The invention relates to a device for cultivating and/or treating cells, especially a bioreactor. Furthermore, the invention relates to a device for pumping a fluid through a device for cultivating and/or treating cells, especially through a bioreactor.

A method and a device of the initially mentioned type is described in an older application of the inventor DE 199 35 643.2.

Meanwhile, it has been found that the formation of a cell layer and cell growth are clearly improved by putting cells under pressure. A known practical approach is to apply a mechanical force to a cell culture chamber, e.g. by a plunger, as described in U.S. Pat. No. 6,060,306. This implies not only high design requirements, but such load does not reflect in-vivo conditions due to the heterogeneous pressure distribution such obtained. The attempt made in U.S. Pat. No. 5,928, 945 is to apply a mechanical force e.g. to cartilage cells chiefly via shear flow stress by means of a culture medium. But this is unphysiological, because no such perfusions are encountered e.g. in articulation areas. In U.S. Pat. No. 6,060, 306, an apparatus is described in which a cartilage construct is moved within a culturing chamber like in a bellows by means of outer wall movements. A disadvantage to said movement processes is that the movement patterns impart high mechanical stress to the membrane structures. That causes the membranes to break after a few days and makes the products insterile and thus inappropriate for implantations.

Furthermore, due to the movement patterns permanently causing convex-concave deformations, the membranes can only generate punctual and thus inhomogeneously distributed pressure deformations. That causes oscillations to form in the culture medium zone and pressure heterogeneities to form in the biological tissues in the bioreactor.

A common characteristic of some of said devices is that the pressure loads are firmly integrated in the culture vessel as a type design. This includes e.g. the bioreactor according to Hoestrup et al. (Tissue Engineering Vol. 6, 1, 2000 pp 75-79) for vessels and heart valves. Such models are a sophisticated design and expensive to sell, because the pumping system, due to its integration in the bioreactor, must be shipped with the future bioimplant as a complete unit. There is no sterile separation from the pump head.

Alternating pressure sources are provided in several other systems such as in WO 97/49799, but not explained in more detail. U.S. Pat. No. 5,899,937 describes a system which can compress a liquid-filled bladder by means of an eccentric movement via a plunger and thus force the liquid out of the bag thereby creating a liquid flow. A bladder is also used in U.S. Pat. No. 5,792,603 (WO 97/49799). But the system comprises vessels leading with open ends into a culture chamber with thorough intermixing of intravascular and extravascular liquids. That is especially disadvantageous if different medium compositions are needed inside and outside the vessels, e.g. to be able to offer growth factors and chemotactic factors directionally. That prevents e.g. the induction of directed migration of myofibroblasts from the place of population towards the outsides and constitutes a significant disadvantage in the population process. Also, that prevents the locally specific repopulation with different cell populations. Another disadvantage is immediate pressure compensation, which makes it impossible to create different pressure profiles in the intravascular and extravascular spaces. In the bioreactor according to Laube et al., the valves are no longer movable already when high volume amplitudes are applied, because the outer walls of the valves need to be fixed to the housing by sewing.

However, the pulsatile or pulse-type flow is in most cases generated in a conventional way via a peristaltic pump such that the pressure amplitudes are rather low in terms of change in volume, show flat frequencies and also mean high stress loads for the hose during several weeks' operation due to the permanent kneading effect. This is true e.g. for Niklason et al., Science 4, 1999 vol 284 pp 489-492, or EP 0320 441.

Further devices are described e.g. in DE 199 15610 A1, which are suitable especially for vessels and heart valves.

BRIEF SUMMARY OF THE INVENTION

The task of the present invention is to provide a device without the above-described disadvantages. An object of the invention is to provide a possibility for generating physiological, homogeneously acting pressure and volume amplitudes equally in a volumetric flow of liquid. Specifically, an object of the invention is to make it possible to generate entirely homogeneous pressure relations in all areas also in the bio-artificial tissue within the bioreactor. The device is to be variably adaptable to the pressure-volume compliance of the system to be perfused. The device is to be modular, small, weight-saving, reliable, of low energy consumption and able to be coupled or combined with any systems to be perfused and is to apply minimal mechanical stress or no mechanical stress at all to the volumetric flow so that it can be connected with blood or other stress-sensitive fluids with or without biological components such as cells or proteins. Another object of the invention is to achieve a high degree of parallelization in the smallest space to be obtained by miniaturizing the module and by the direct ability to be coupled to and integrated in any possible perfusion systems.

In the present description, the term fluid is meant to designate not only liquids, especially blood, nutrient solutions, oils, or technical solutions, but also gases.

Other features which are considered as characteristic for the invention are set forth in the appended claims.

Although the invention is illustrated and described herein as embodied in "device for pressurized perfusion especially for culturing and/or treating cells", it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 13a through 13c show another embodiment of a device for pumping fluids according to the present invention, FIG. 15 shows another embodiment of a device for pumping fluids according to the present invention.

DETAILED DESCRIPTION OF THE INVENTION

Figure 1:
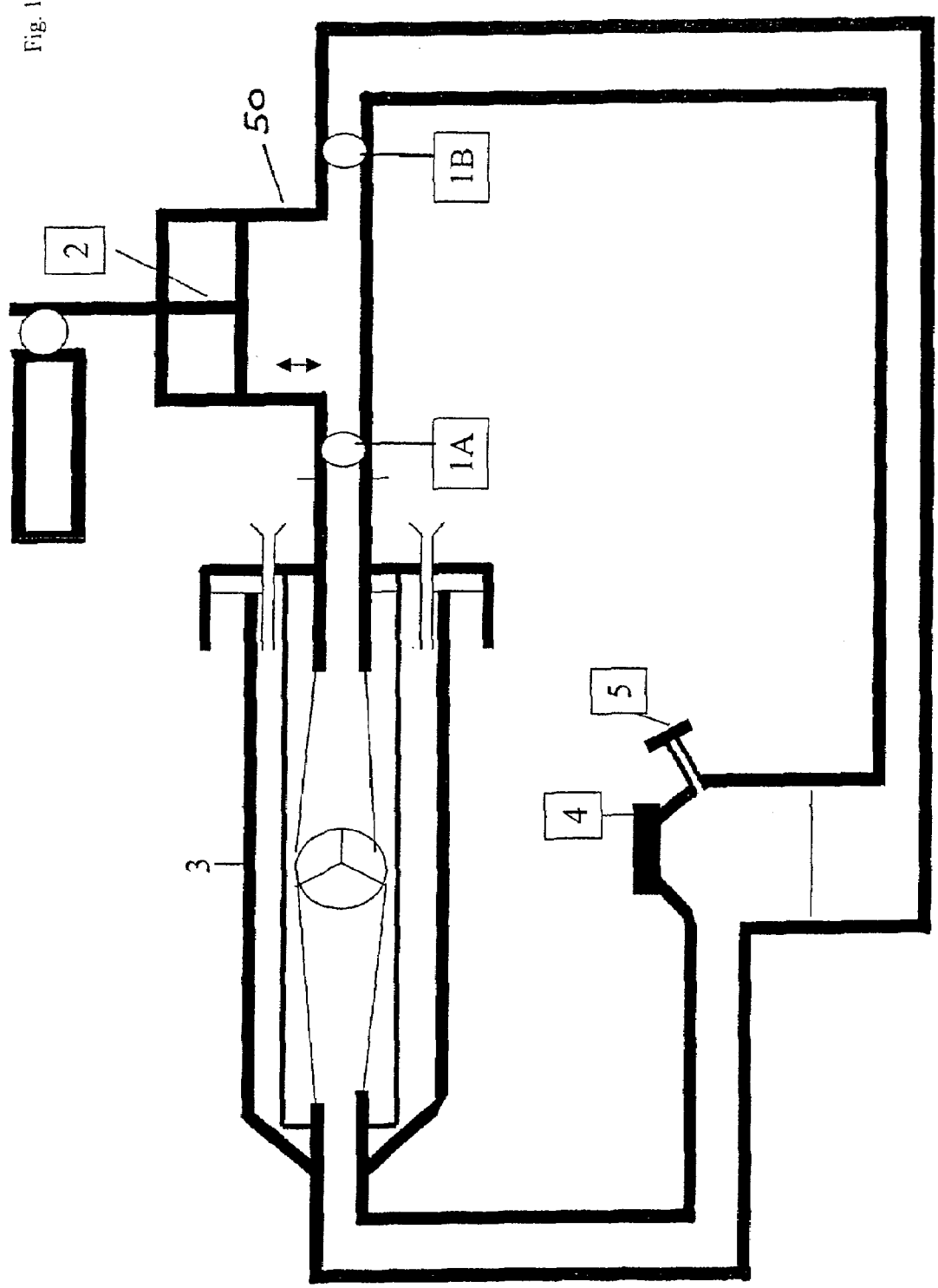
FIG. 1 shows a first embodiment of a device for pressurized perfusion according to the present invention.

FIG. 1 shows a modular component, which is coupled to a bioreactor 3. The module is composed of two valves 1A and 1B as well as of a piston2 and is adaptable to the bioreactor via a sterile coupling and directly, as shown in FIG. 1, integratable in the influence area. Both valves 1A and 1B open in the same direction, in FIG. 1 to the left, towards the bioreactor. This generates a volumetric flow which is introduced into the reactor area at a high amplitude and pressure curve. So it is possible to achieve the opening and closing of an implant placed in the bioreactor, e.g. an allogenic heart valve. Two-leaflet valves opening or closing passively from flow changes are especially suited for the valves 1A and 1B. Other non-return valves, such as balls in a conically tapered tube section, are also possible.

FIG. 1 shows the perfusion module in a sagitally directed form. The advantage is that the backward movement of the piston2 across the opening of valve 1A enhancedly causes the heart valve leaflet to close and thus also allows the bioreactor to be emptied. The forward movement of the piston2 causes the valve 1B to close and the valve 1A to open with subsequent opening of the biovalve in the bioreactor. During the backward movement of the piston2, fluid or medium is taken in from the reservoir 4 thereby filling the chamber in the perfusion module. The latter is refilled in circuit. Pressure compensation is via a sterile filter 5.

Figure 5:
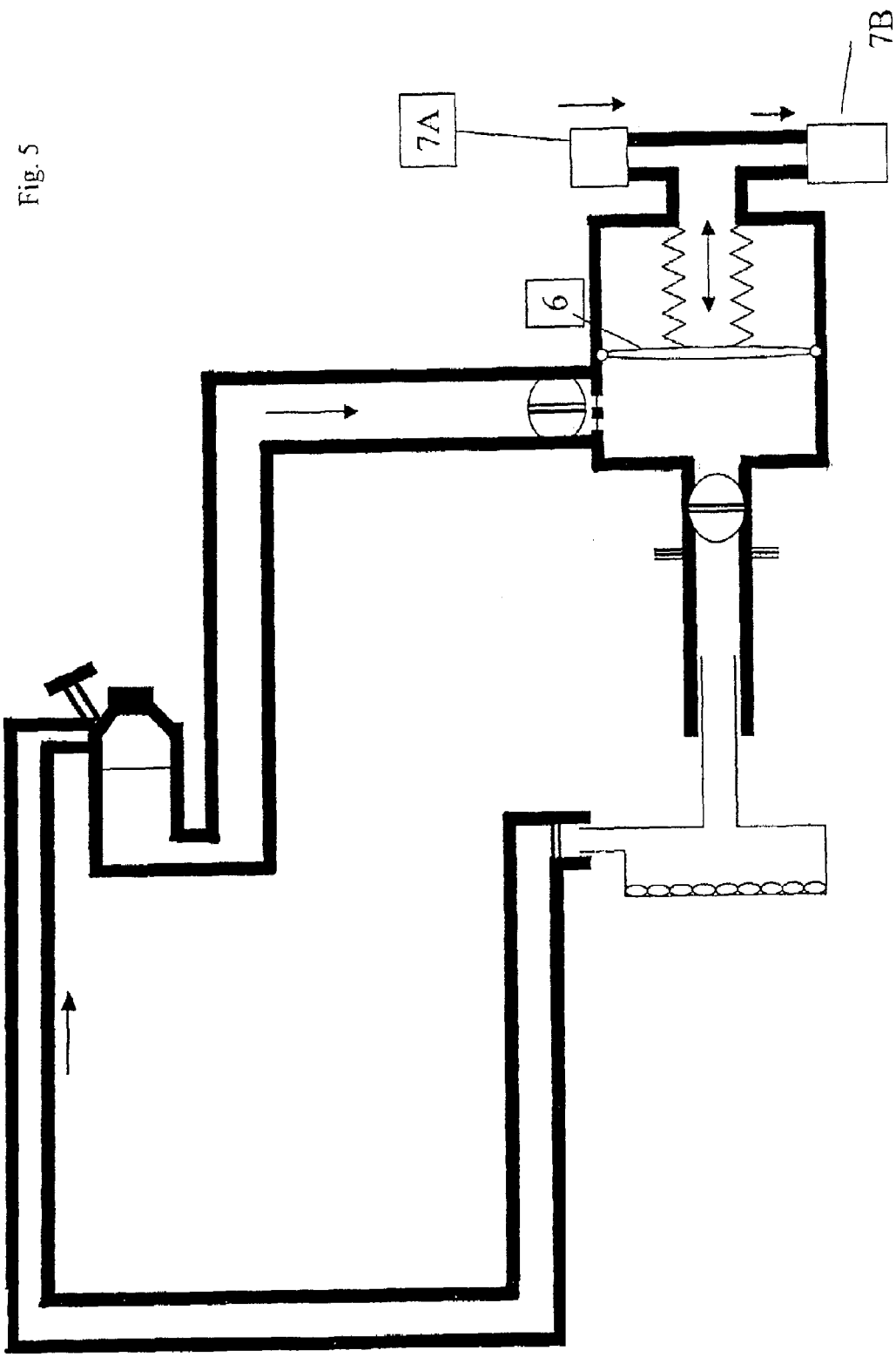
FIG. 5 shows a fifth embodiment of a device for pressurized perfusion according to the present invention.

FIG. 5 shows that the changes in volume in the perfusion module can also be achieved by displacing a plate 6, which can be moved alternately by means of compressed air or vacuum via two valves 7A and 7B. The advantage is that the classical and sophisticated piston technology is done away with. The latter also requires an additional outer motor as shown in FIG. 1.

Figure 2:
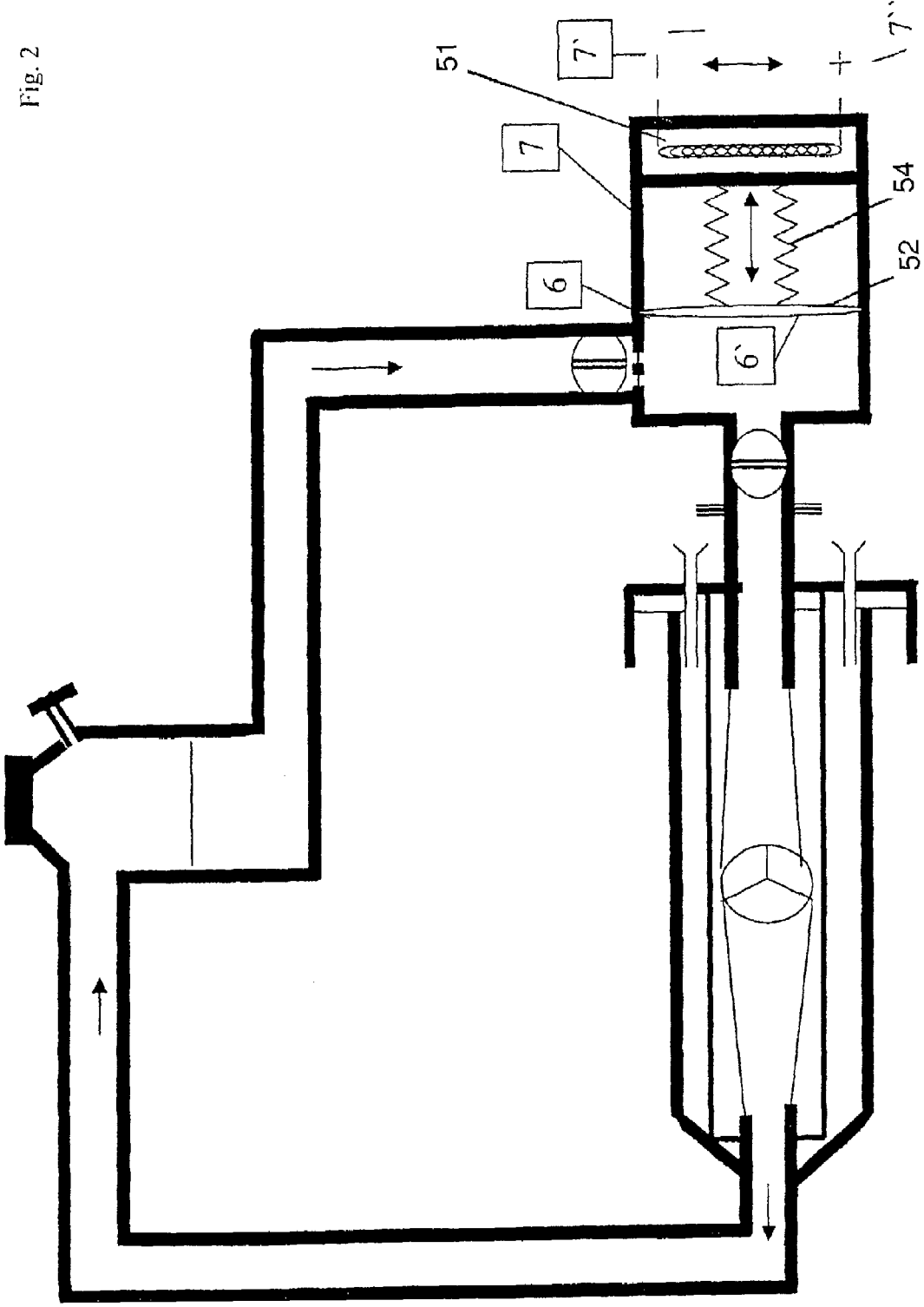
FIG. 2 shows a second embodiment of a device for pressurized perfusion according to the present invention.

The device according to FIG. 2 is even compacter in construction, in which the movable plate 6 is a permanent magnet with a biocompatible or liquid-proof or non-erosive encapsulation with e.g. a plastic layer of silicone or Teflon 6' able to simultaneously provide a sealing function. Also, a jacket with a further metal (e.g. titanium, highgrade steel) can be provided. A sealing ring of e.g. Teflon or silicone is combinable for this purpose. But what is essential is that an alternately attracting or repelling force field can be created on the permanent magnet by integration of a current coil used to alternately generate negative poles 7' or positive poles 7". As an alternative to using permanent magnets, it is possible to integrate paramagnetic particles in the plate 6 so that a yet better directionalization can be achieved with regard to the force field of coil 7. But the advantage of the mechanical principle is that costly external motors or compressed air or vacuum systems like those as still described herein in combination with perfusion technology can be done away with. Only then, the entire module will become very small, because the force-generating module or module responding to external forces is integrated in the movement module. Just a current source and a conventional electronic control are needed.

Figure 3:
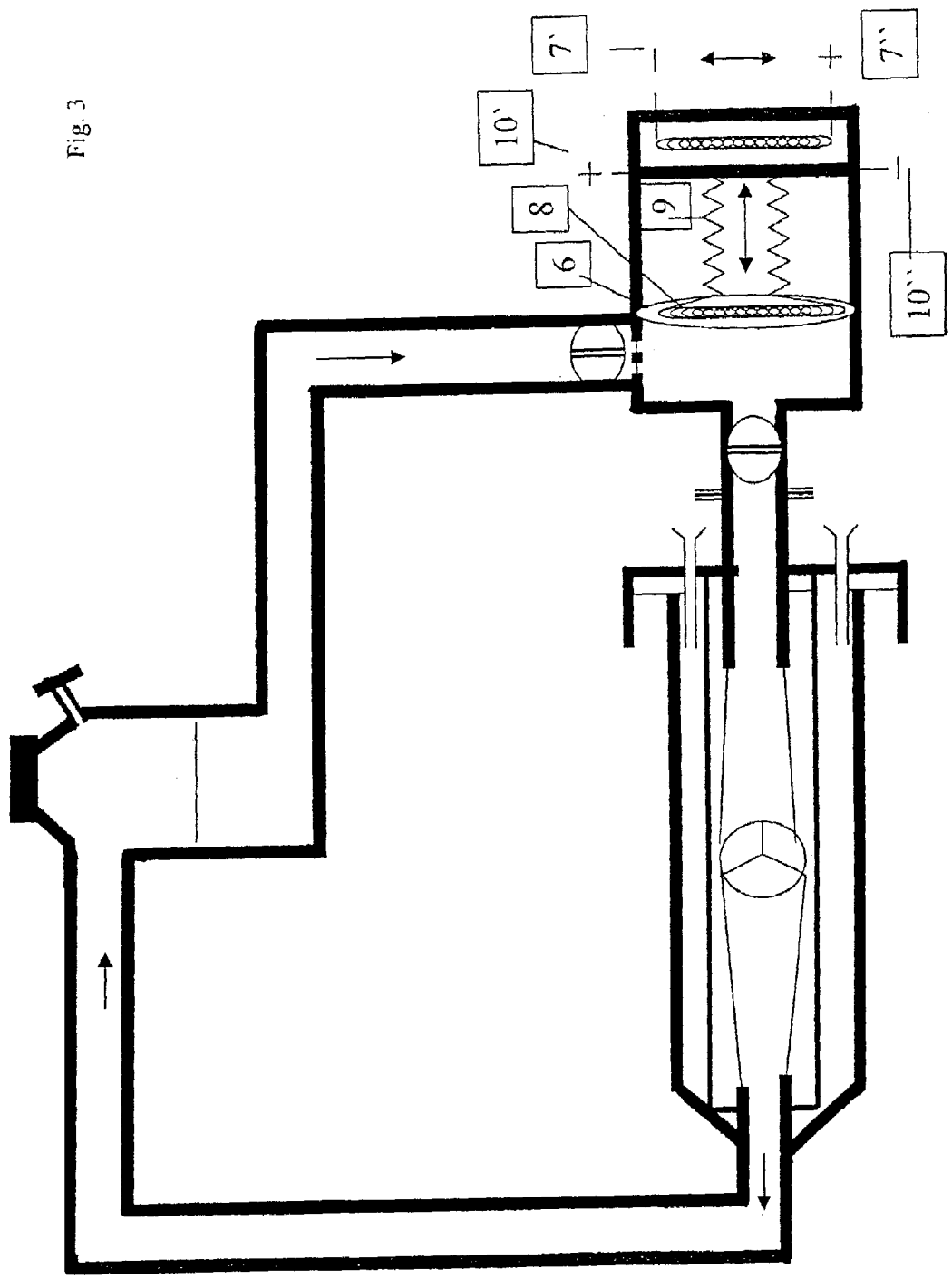
FIG. 3 shows a third embodiment of a device for pressurized perfusion according to the present invention.

FIG. 3 shows that the plate 6 can have its own integrated electric coil 8, which is connected via an elastic cable connector to a current source 10' and 10" alternately polarized to 7' and 7".

Figure 4:
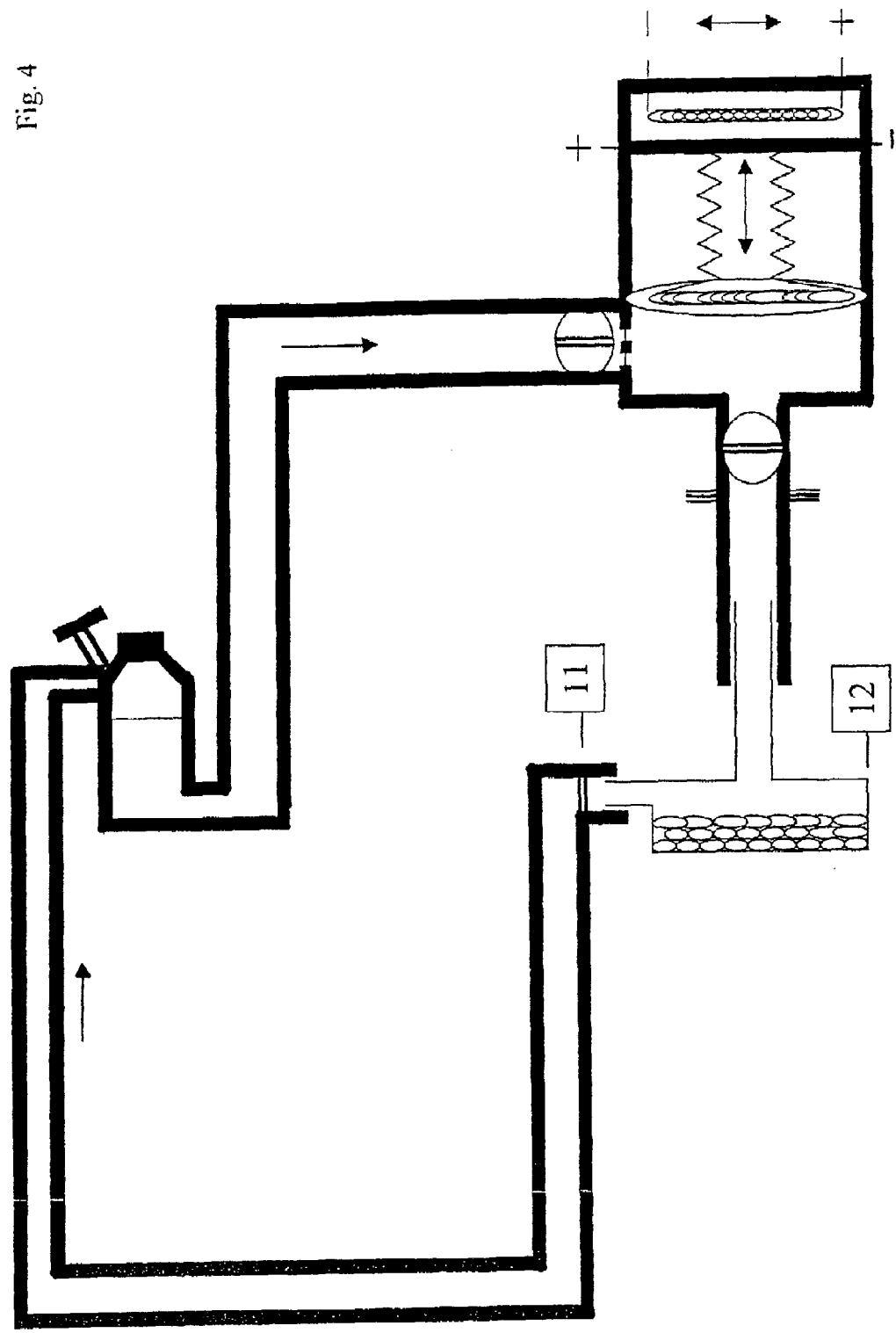
FIG. 4 shows a fourth embodiment of a device for pressurized perfusion according to the present invention.

FIG. 4 shows how a cartilage-cell/bone-cell bioreactor 12 is integrated in the circuit. Stem cell integration is also possible here. Due to the use of a stop valve 11, a pressure increase coupled with a volumetric flow is realizable. This is particularly important for the differentiation of cartilage but also bone structures, as well as of combinations, e.g. by using pure-phase beta-tricalcium phosphates as a seeding basis.

Figure 6:
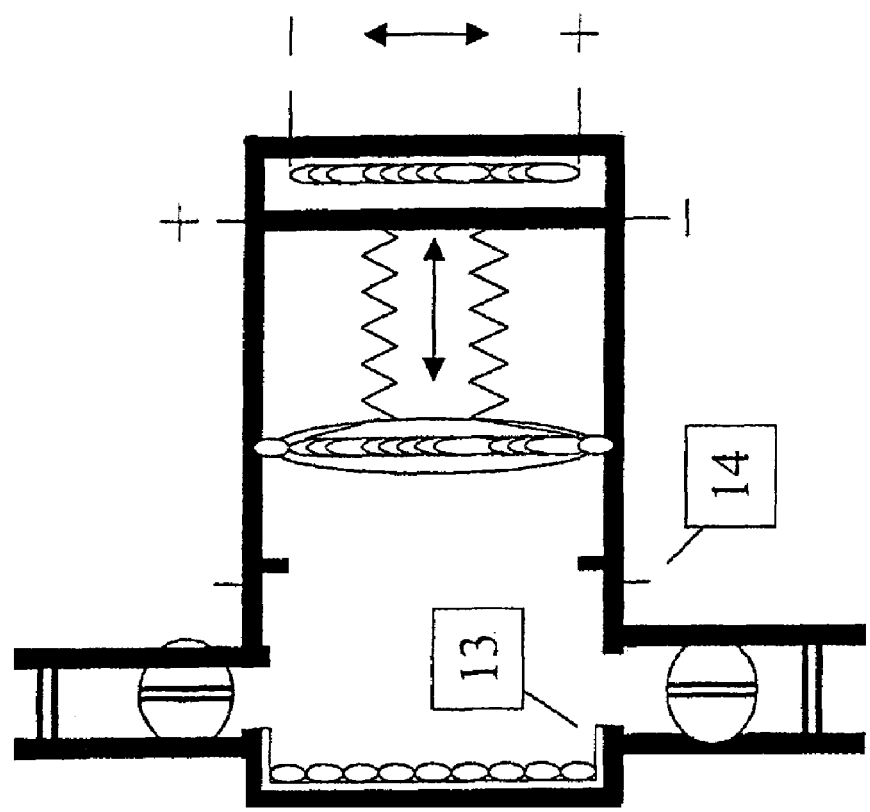
FIG. 6 shows a sixth embodiment of a device for pressurized perfusion according to the present invention.

FIG. 6 shows an integrative system in which the magnetic perfusion principle is integrated in a bioreactor for the production of cartilage structures. The advantage is that the construction of the system is simpler in terms of apparatus while maintaining controlled physiological pressure amplitudes and volumetric flows. In this case, the cell culture can be located in a removable insert 13. The piston can be lowered down to the insert 13 so as to be able to apply also immediate mechanical pressure to the cartilage structures. In addition to that, the system thus is emptied entirely so that mixing processes in the culture system can be directly controlled in terms of volume in order to be able to define the growth factor concentrations in situ. For the removal of the insert, the bioreactor can be opened or closed at 14 by means of e.g. a rotary or a clamp-type lock.

Figure 7:
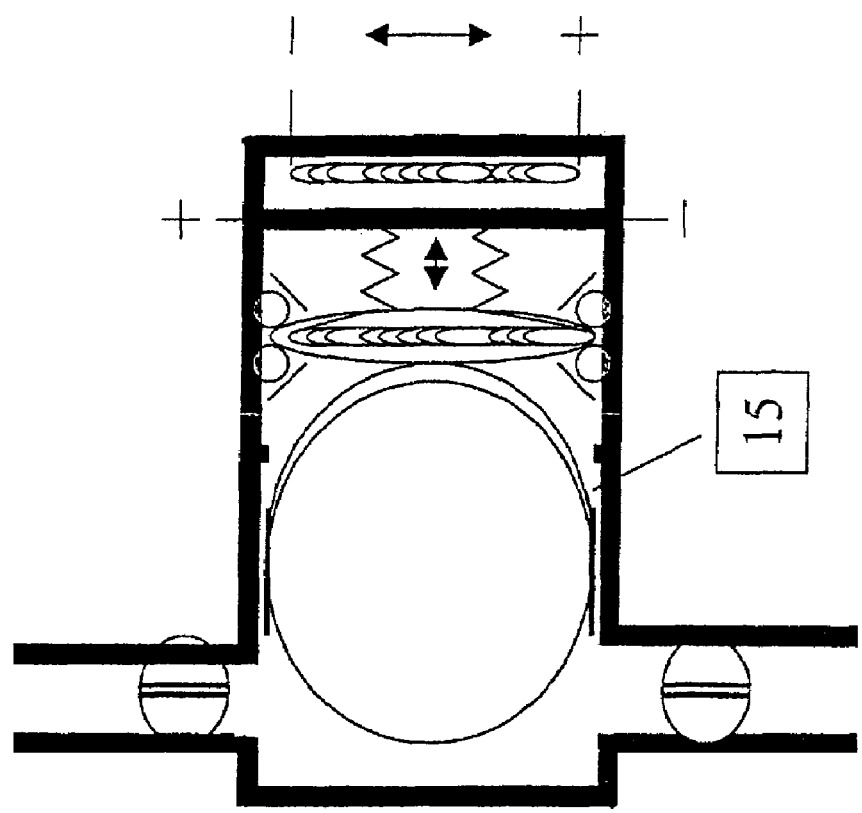
FIG. 7 shows an embodiment of a device for pumping fluids according to the present invention.

FIG. 7 shows the use of a magnetic pumping mechanism for imparting movement to a membrane thereby creating a volumetric flow.

Figure 8:
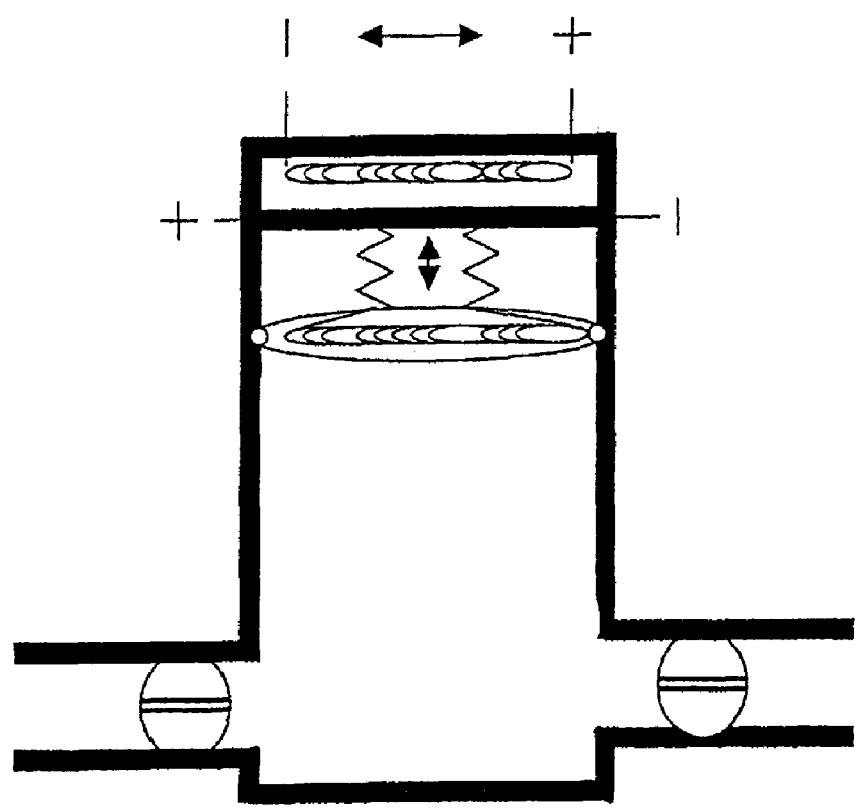
FIG. 8 shows another embodiment of a device for pumping fluids according to the present invention.

FIG. 8 shows the use of a magnetic pumping system for pumping liquids such as blood, aqueous solutions or gases without supplying a treatment module such as a cell culture system (e.g. a bioreactor). An application is e.g. extracorporal perfusion for heart-lung machines or for assisting liver transplantation operations after hepatectomy. Previous rotary pumps produce even volumetric flows, but their manufacture is very costly and sophisticated. Using the pumping principle according to the invention in extracorporal perfusion has the advantage of restituting physiological pressure amplitudes.

They are important for preserving organ functions and cellular differentiation especially in longer-term use.

Figure 9:
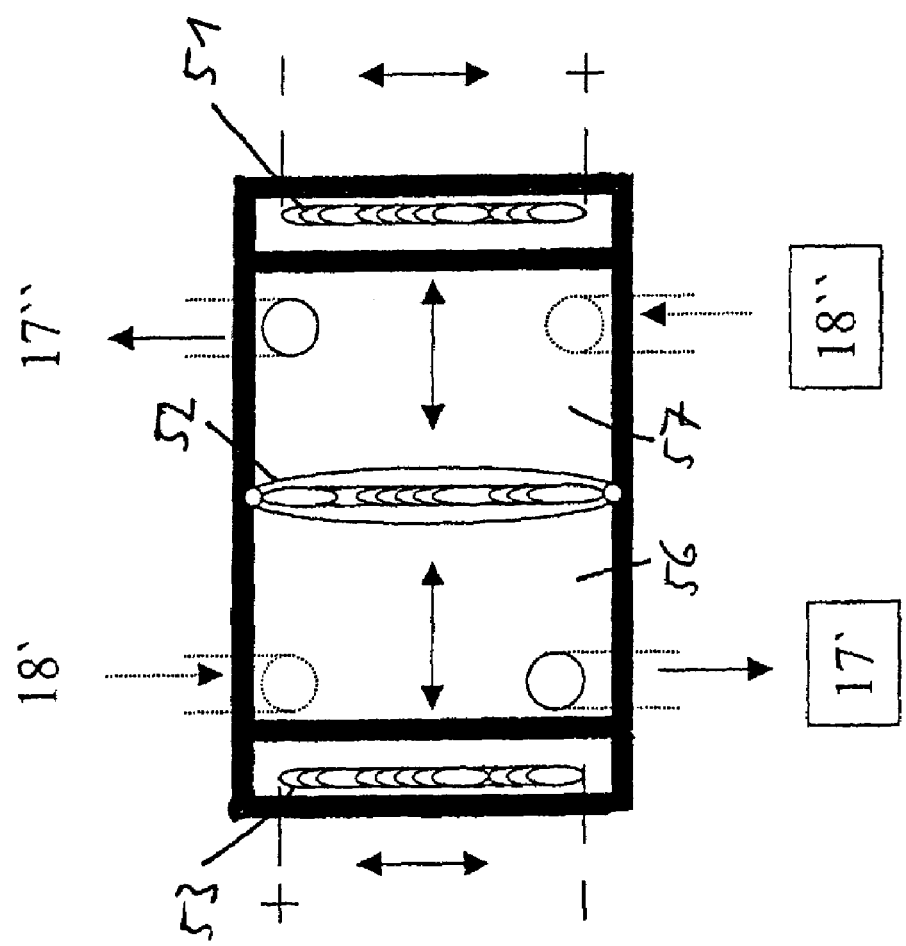
FIG. 9 shows another embodiment of a device for pumping fluids according to the present invention.

FIG. 9 shows a double-sided pumping chamber. The plate 16 moves in the chamber in an oscillating manner and each of the outlet openings 17' and 17", which are coupled to valves, is controlled in a direction opposite to the inlet openings 18' and 18". In the centre, there is again a movable plate with a permanent magnet, paramagnet, or a magnetismsensitive material, or an electric coil.

Figure 10:
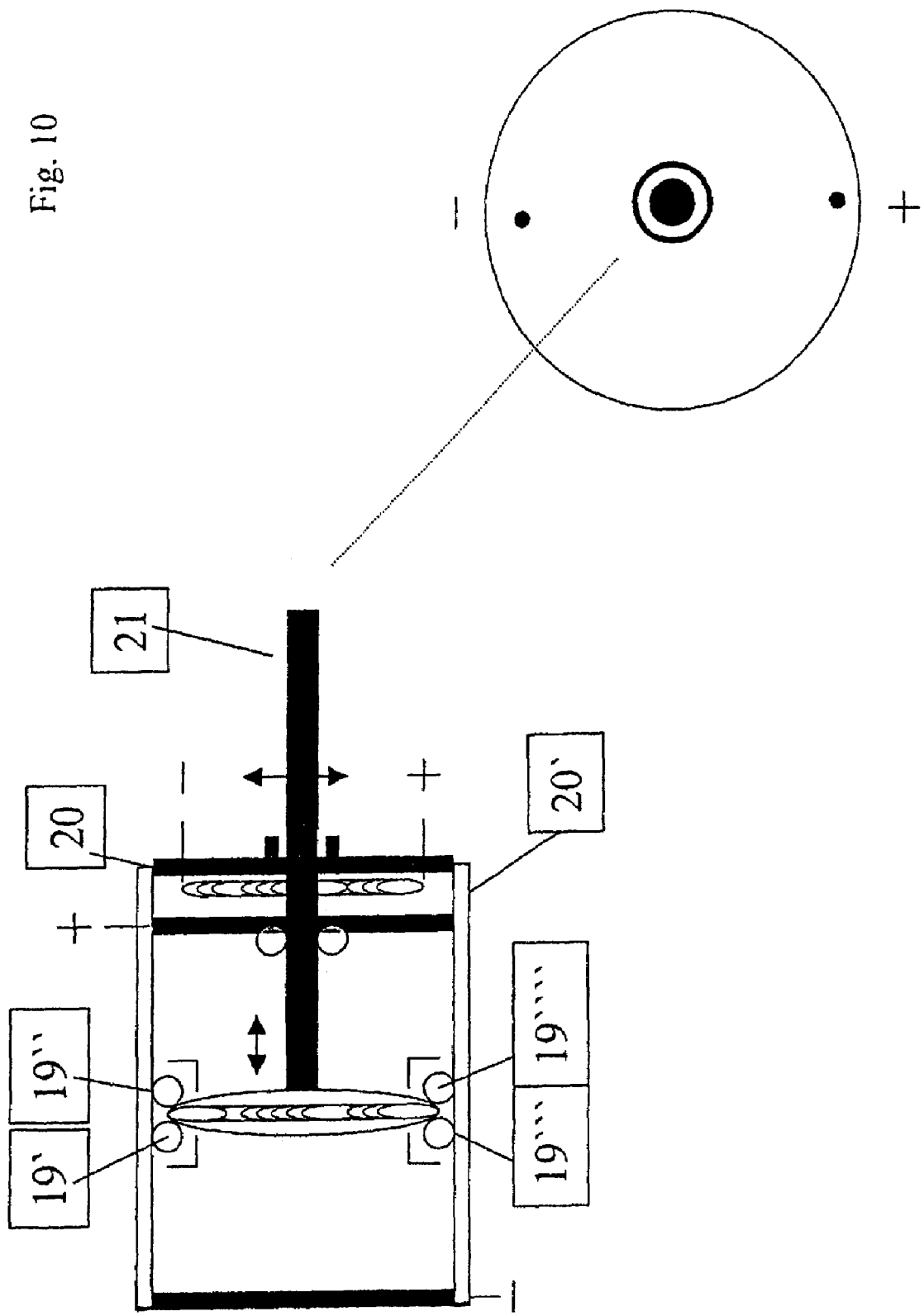
FIG. 10 shows another embodiment of a device for pumping fluids according to the present invention.

FIG. 10 shows the construction for a piston motor. In this case, the plate is supported the rollers 19' through 19"" and moves in a chamber. The inner surfaces of the chambers 20' and 20" are equipped with electric conductors, which via the rollers 20' through 20"" come in contact with the plate 6, within which an electric coil is again located. The plate 6 is equipped with a rod, which transfers the force of movement like a piston towards the outside. This can be used in vehicles or as a substitute for classical combustion engines.

Figure 11:
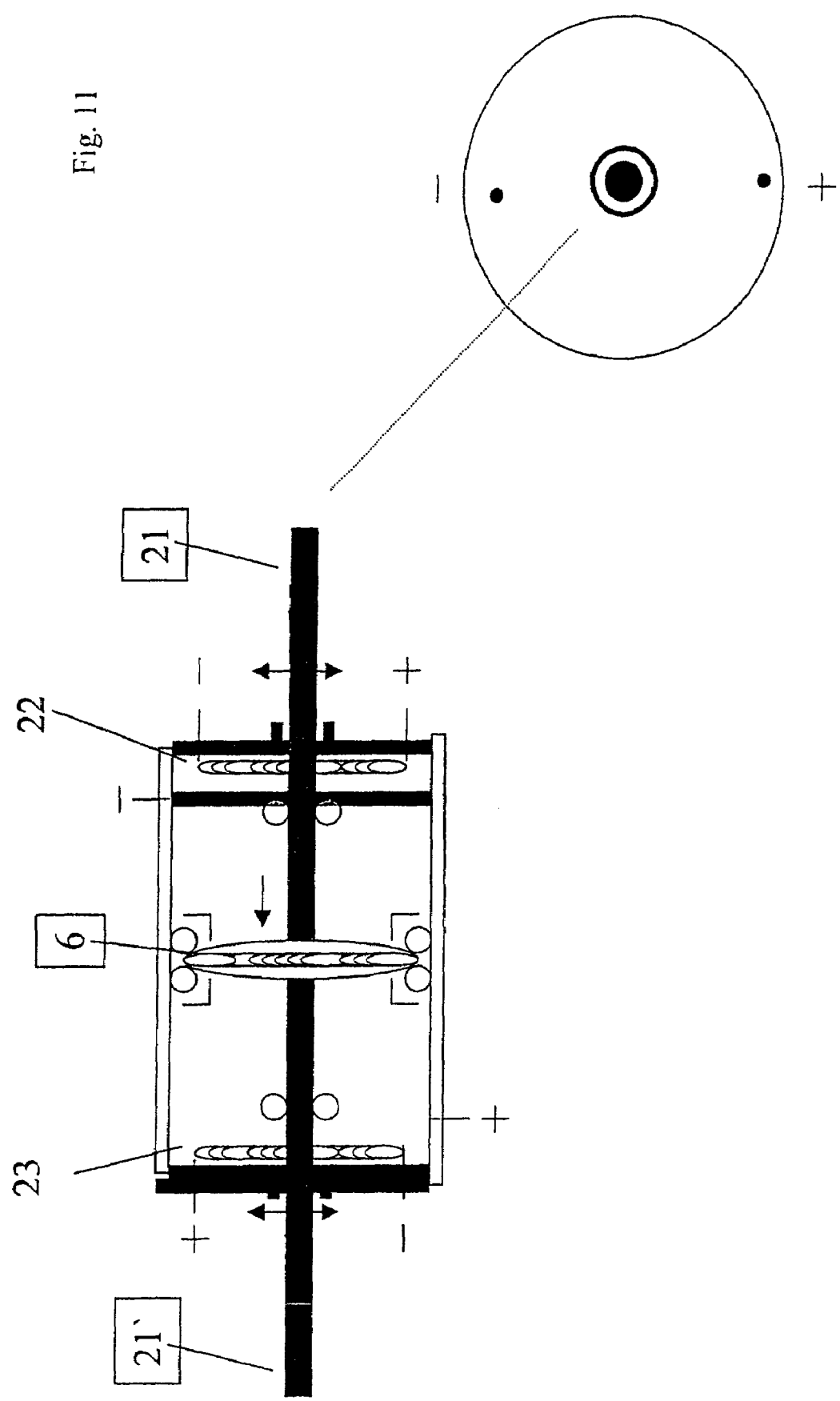
FIG. 11 shows another embodiment of a device for pumping fluids according to the present invention.
Figure 12:
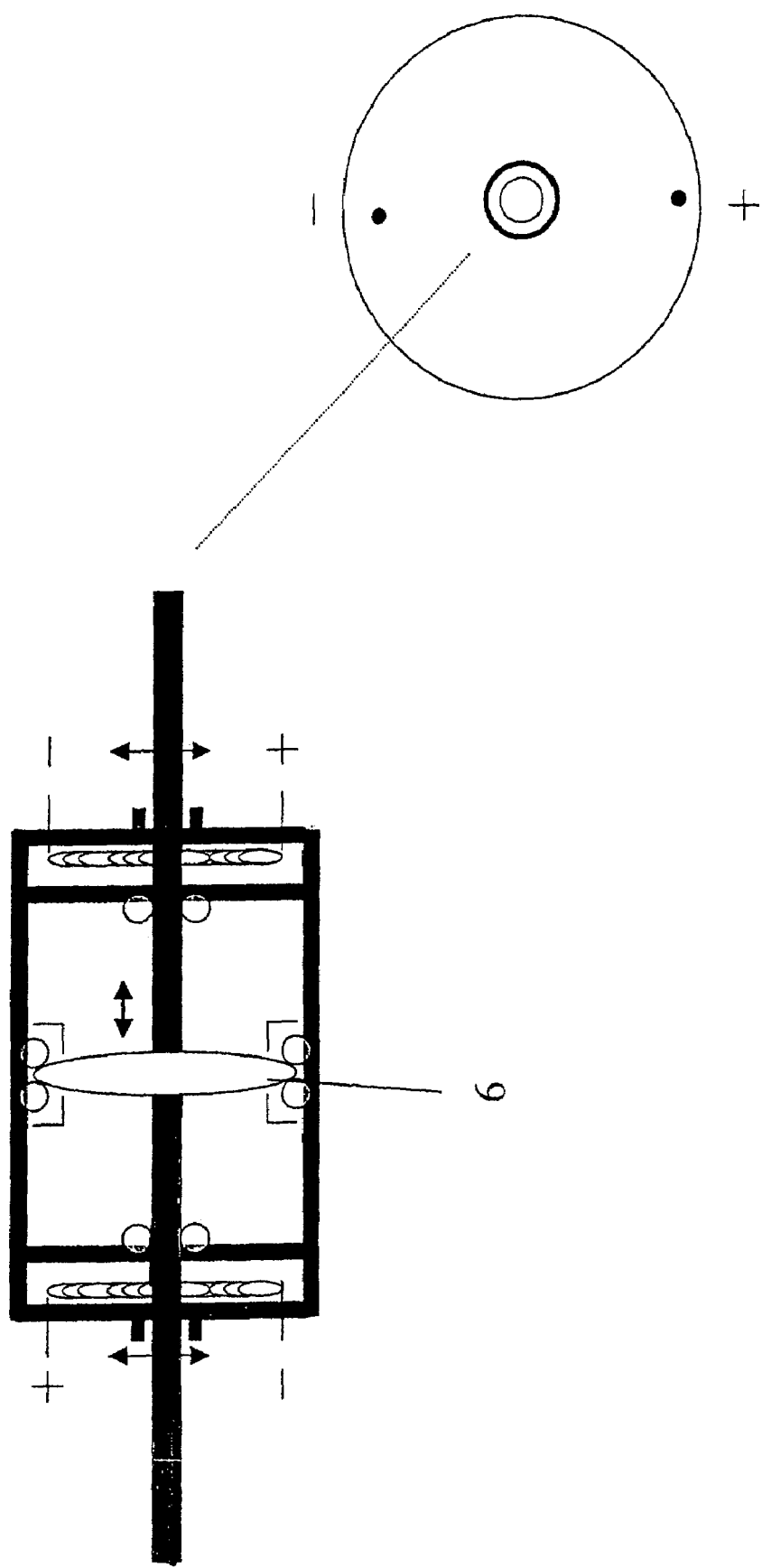
FIG. 12 shows another embodiment of a device for pumping fluids according to the present invention.

FIG. 11 represents the same principle as FIG. 10, but this time both an extension direction and a compression direction are possible simultaneously for the pistons 21 and 21'. In this case, the electric magnetic fields in 22 and 23 can always be oriented in directions opposite to one another and the magnetic field in the plate (plunger) 6 remains unchanged. As an alternative, the field in 6 can constantly alternate with the fields in 22 and 23 remaining unchanged. The coil in the plate 6 is supplied with current, like in FIG. 10, through the roller mechanism 19'-19"". FIG. 12 relates to how a permanent magnet is used in plate 6.

FIG. 13 shows an embodiment in which the magnetic pumping mechanism located in an elastic tube, such as in a hose, is directly installed in the wall structures either as half-shells or as attachments to be fixed or to be integrated. The advantage is to provide a universal pumping module that is directly integratable in circuits or in hose or tube systems. In FIG. 13a, half-shells 24 and 25 are shown, which are connected with the wall of the hose system through elastic plastic materials. Said materials can be composed of conventional elastic tapes or can also have a direct integration in the wall structure of the hose. Additional coils 26 and 27 can be installed on the outside in order to increase the pumping force. So the internally movable pump in combination with the passively movable valves 1A and 1B is a universally applicable pumping element.

The very gentle treatment of the internal perfusate also allows it to be installed in the body as a heart-assisting system in combination with a battery (internal) or a magnetic field, which is installed outside on the body (e.g. thorax). Force transmission inwards to the implant is not invasive and without mechanical stress for the body. For implants, it is wise to integrate permanent magnets or so-called paramagnets in (nano-)particle form in the wall structures of the hose implant in a way to be able to achieve a contraction of the hose volume by changing the external magnetic field direction. For this purpose, the external poles can be arranged controlaterally, i.e. in front of and behind the thorax. The FIGS. 13b and c show how an external battery unit 28, 29 is installed around a hose 27 with 2 movable plates 6 and 6', which lead to passive changes of volume of the hose 6 (sic!, the translator).

Figure 14:
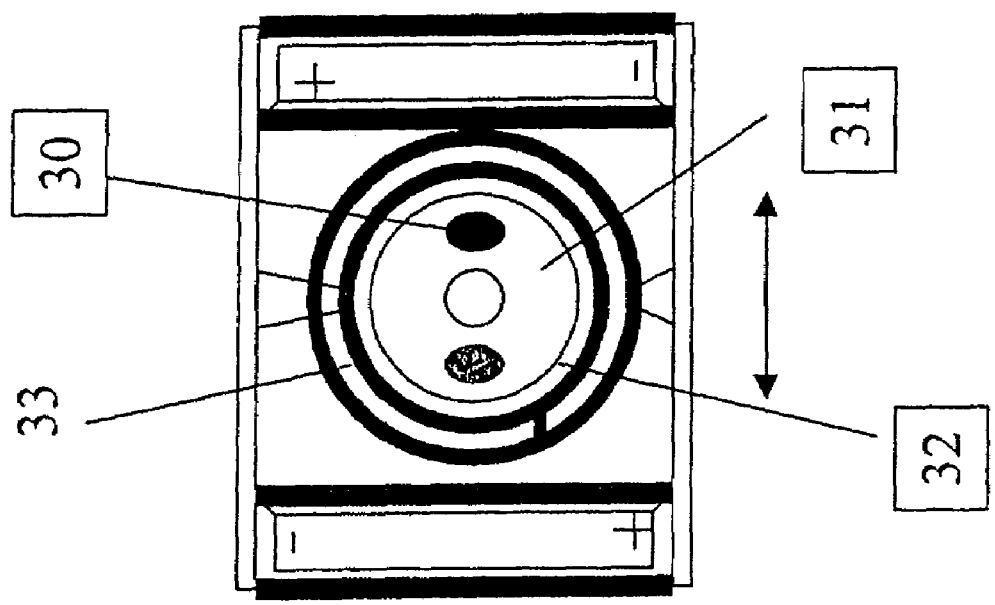
FIG. 14 shows another embodiment of a device for pumping fluids according to the present invention.

In FIG. 14, it is shown how magnetic or magnetizable rods 30 are integrated in the wall structure 31 of a hose 32. A circumferentially installed electric coil generates an inner magnetic field causing passive changes in volume in hose 32. The hose is surrounded by an electric coil 34.

FIG. 15 shows an electric coil 34 integrated in the hose itself. There is an electric coil 33 installed on the outside.

Another simplification is the introduction or the elastic jacketing of a hose with an elastic coil 35. Changing the electric flow directions will cause field changes and thus cause the elastic coil rings to attract or repel one another. The connection with the elastic hose leads to pumping processes, which can again be directionalized by passive valves.

Figure 16:
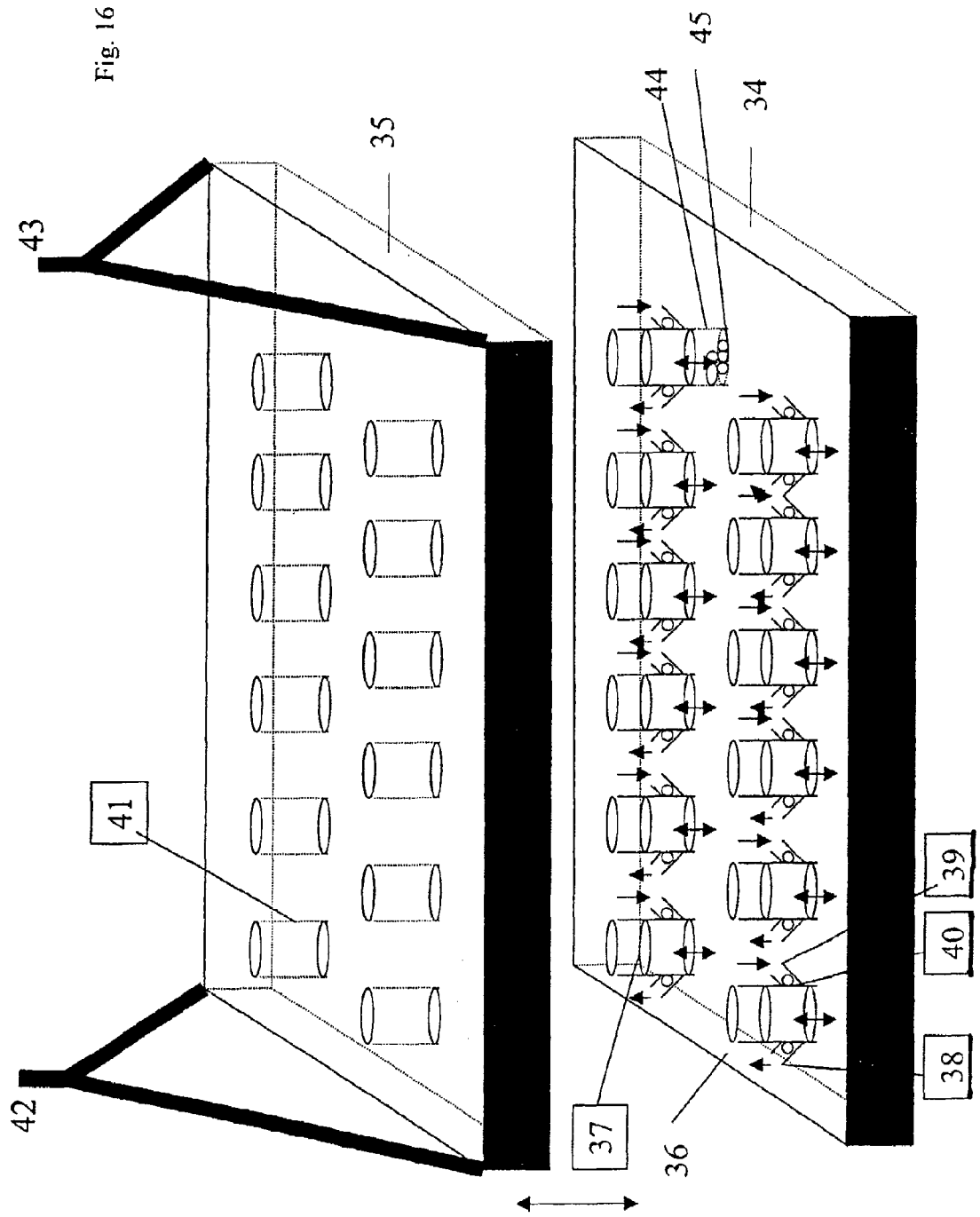
FIG. 16 shows an embodiment of a device for pressurized perfusion according to the present invention.

FIG. 16 shows an example for parallelization. For this purpose, e.g. miniaturized pump modules 36 are placed on chambers 44, which can contain cell cultures 45. The volume in the chambers is equivalent to e.g. 200-500 .mu.l and contains primary cells in reconstructed tissue section cultures. The plate 37, which can be attracted and repelled magnetically, can move up and down directionally in the pump module. A movement away from the cell culture chamber or from the reaction chamber 44 provided for reaction without cellular systems causes the valve 40 to open and fresh medium is introduced by way of volume increase into the reaction chamber 44. The reversing movement increases the internal pressure in the reaction chamber and causes the valve 38 to open so that a volumetrically definable portion of the reaction chamber contents can be forced out. The advantage of this mixing process, e.g. in cell culture, is that portions of the cytokines and growth factors produced in situ by the cells and enriched therewith can remain in the chamber despite the feeding of fresh medium. This culturing approach is gentler than the complete replacement of nutrient liquid. So this technology allows locally defined mixing to be achieved even for batchwise nutrient processes, i.e. for the first time also in non-recirculating systems. This makes it possible to combine the advantages of non-recirculating systems, such as meterability as well as definability and programmability, especially for pharmacological studies in minisystems, with the cell-biological advantages of largest possible biological milieu constancy. The vertical movements of the intermediate plates 37 can be caused by appropriate positioning and vertical movement of a cover plate structure 35, which houses accordingly positioned magnets or coils. Operation is possible also with a fixed cover plate structure 35, if in such case changing orientations of magnetic fields in said structure are induced by changing current flows in electric coils.

Figure 17:
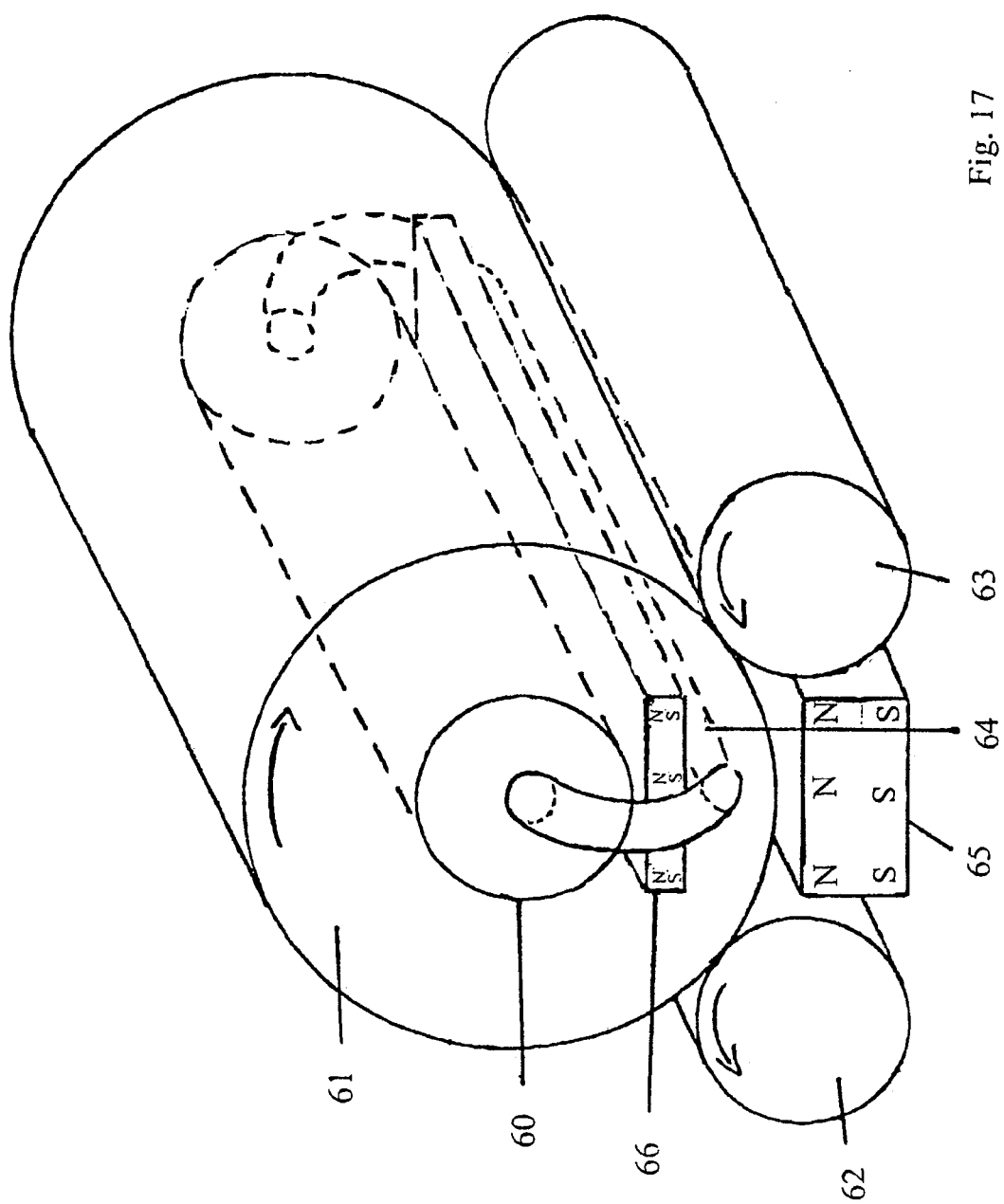
FIG. 17 shows an embodiment of a device for pressurized perfusion according to the present invention.

FIG. 17 represents a further embodiment of the invention, which comprises a culture bottle or bioreactor 60 with a cylindrical shape. The culture bottle is surrounded by a jacket 61, which is made up of an elastic material, especially a plastic or rubber material, and has a cylindrical shape too. The culture bottle 60 with its jacket rests on the rollers 62, 63, which are rotated by a drive not shown.

The jacket 61 is provided with a hollow space 64, which is limited by valves in the area of the end faces of the cylindrical jacket to interact with them and thus act as a pump through a change in volume. Advantageously, the change in volume can be achieved by permanent magnets with one permanent magnet 66 located in the jacket between the hollow space 64 and the culture bottle 60 and a second permanent magnet 65 beneath the jacket 61. So the hollow space 64 is compressed when the permanent magnet 64 enters its lower position, because the magnets are arranged such that they attract one another in said position with the compression being assisted by the dead weight of the permanent magnet 66. The hollow space is on the contrary compressed when the permanent magnet is in its upper position. So the pumping effect is eventually achieved in a simplest way by the drive for the running rollers 62, 63. They are connected with the hollow space 64 through hoses at the end faces of the culture bottle so that the fluid can circulate between the culture bottle and the hollow space in a batchwise flow initiated by the rotating movement of the apparatus.

As an alternative to the embodiment according to FIG. 17, it is also possible to do without the permanent magnet 65 and replace the permanent magnet 64 by a weight. But another possibility is to replace the permanent magnet 66 by an electromagnet.

The invention claimed is:

1. A bioreactor suitable for pressurized perfusion cultivation of cells, the reaction chamber of which is coupled to or integrated with the chamber of a pump unit that is able to generate a discontinuous or batch-wise delivery flow of a fluid running in circuit, said pump unit comprising:
   a cylinder;
   a piston including a plate that is movable within the cylinder in its axial direction;
   valves located on a downstream side and an upstream side of said cylinder, for backflow prevention;
   said plate including a first magnet, which is provided with an elastic bearing in form of an elastic bellows with convolutions or a compression spring or a tension spring, and a second magnet is arranged at one end of the cylinder so as to achieve a displacement of the piston in combined action with the first magnet, thus generating said delivery flow.

2. The bioreactor of claim 1, wherein said first and/or said second magnet is a permanent magnet or an electromagnet.

3. The bioreactor of claim 1, wherein at least said first and/or said second magnet is an electromagnet, whose alternating magnetic field causes the piston in the cylinder to move back and forth along the cylinder axis.

4. The bioreactor of claim 3, wherein said first electromagnet located at the plate of the piston via current lines within the elastic bellows.

5. The bioreactor of claim 1, wherein said cylinder is provided with an inner membrane that seals the cylinder chamber in which said piston moves.

6. The bioreactor of claim 1 provided with a reservoir for nutrient solution.

7. The bioreactor of claim 1, wherein an interior space of the pump housing can be used for culturing cells in a way that the pumping chamber of the cylinder and the chamber of the bioreactor are coincident.

* * * * *